US008094304B2

(12) United States Patent
Raicu et al.

(10) Patent No.: US 8,094,304 B2
(45) Date of Patent: Jan. 10, 2012

(54) TWO-PHOTON MICROSCOPE WITH SPECTRAL RESOLUTION

(75) Inventors: Valerica Raicu, Shorewood, WI (US); Russell Fung, Milwaukee, WI (US)

(73) Assignee: UWM Research Foundation, Inc., Milwaukee, WI (US)

( * ) Notice: Subject to any disclaimer, the term of this patent is extended or adjusted under 35 U.S.C. 154(b) by 0 days.

(21) Appl. No.: 13/028,803

(22) Filed: Feb. 16, 2011

(65) Prior Publication Data
US 2011/0134232 A1 Jun. 9, 2011

Related U.S. Application Data (63) Continuation of application No. 11/904,860, filed on Sep. 28, 2007.

(60) Provisional application No. 60/848,351, filed on Sep. 29, 2006.

(51) Int. Cl.
*G01J 3/30* (2006.01)
(52) U.S. Cl. ........................................ 356/318
(58) Field of Classification Search .................. 356/300, 356/318
See application file for complete search history.

(56) References Cited

U.S. PATENT DOCUMENTS

| 5,034,613 | A | 7/1991 | Denk et al. |
|---|---|---|---|
| 5,192,980 | A | 3/1993 | Dixon et al. |
| 6,134,002 | A | 10/2000 | Stimson et al. |
| 6,344,653 | B1 | 2/2002 | Webb et al. |
| 6,388,746 | B1 | 5/2002 | Eriksson et al. |
| 6,809,815 | B2 | 10/2004 | Knebel |
| 2002/0198457 | A1* | 12/2002 | Tearney et al. ............... 600/476 |
| 2007/0247620 | A1* | 10/2007 | Koo ............................. 356/301 |
| 2007/0296973 | A1 | 12/2007 | Kiers et al. |

OTHER PUBLICATIONS

Denk, Winfried, et al., "Two-Photon Laser Scanning Fluorescence Microscopy", Science, New Series, vol. 248, No. 4951, pp. 73-76, Apr. 6, 1990.
Haraguchi, Tokuko, et al., "Spectral Imaging Fluorescence Microscopy", Genes to Cells, vol. 7, pp. 881-887, 2002.
Stimson, Michael, J., et al., "A Unique Optical Arrangement for Obtaining Spectrally Resolved Confocal Images", Review of Scientific Instruments, vol. 70, No. 8, pp. 3351-3354, Aug. 1999.
Bacskai, B. J., J. Skoch, et al. (2003). "Fluorescence resonance energy transfer determinations using multiphoton fluorescence lifetime imaging microscopy to characterize amyloid-beta plaques." Biomed Opt. 8: 368-375.

(Continued)

*Primary Examiner* — Tarifur Chowdhury
*Assistant Examiner* — Abdullahi Nur
(74) *Attorney, Agent, or Firm* — Michael Best & Friedrich LLP (57) ABSTRACT

A microscope for generating an image of a sample, the microscope includes a light source for generating a pulsed light; an optical scanner receiving the pulsed light and transmitting the pulsed light to the sample to be imaged causing the sample to emit energy; a dispersive element that receives the emitted energy from the sample, disperses the energy into its spectral elements and transmits the spectrally dispersed energy; and a camera that generates a spectrally resolved image of the sample based on the spectrally dispersed energy from the dispersive element. Also described is a method of generating spectrally resolved images of the sample.

21 Claims, 7 Drawing Sheets

OTHER PUBLICATIONS

Elangovan, M., R. N. Day, et al. (2002). "Nanosecond fluorescence resonance energy transfer-fluorescence lifetime imaging microscopy to localize the protein interactions in a single living cell." J. Microsc 205 (Pt 1): 3-14.

Greenbaum, L., D. Schwartz, et al. (2002). "Spectrally resolved microscopy of GFP trafficking." J. Histochem. Cytochem. 50(9): 1205-12.

Lansford, R., G. Bearman, et al. (2001). "Resolution of multiple green fluorescent protein color variants and dyes using two-photon microscopy and imaging spectroscopy." J. Biomed. Opt 6(3): 311-318.

Neher, R. and E. Neher (2004). "Optimizing imaging parameters for the separation of multiple labels in a fluorescence image." J. Microsc 213 (Pt 1): 46-62.

Neher, R. A. and E. Neher (2004). "Applying spectral fingerprinting to the analysis of FRET images." Microsc. Res. Tech. 64(2): 185-195.

Raicu, V, (2007). "Efficiency of Resonance Energy Transfer in Homo-Oligomeric Complexes of Proteins." Journal of Biological Physics 33: 109-127.

Raicu, V., D. B. Jansma, et al. (2005). "Protein interaction quantified in vivo by spectrally resolved fluorescence resonance energy transfer." Biochem J. 385 (Pt 1): 265-77.

Raicu, V., M. R. Stoneman, et al. (2009). "Determination of supramolecular structure and spatial distribution of protein complexes in living cells." Nature Photonics 3(2): 107-113.

Zipfel, W. R., R. M. Williams, et al. (2003). "Nonlinear Magic: Multiphoton Microscopy in the Biosciences." Nat Biotechnol 21: 1369-1377.

* cited by examiner

TWO-PHOTON MICROSCOPE WITH SPECTRAL RESOLUTION

RELATED APPLICATIONS

The present patent application is a continuation of U.S. patent application Ser. No. 11/904,860 filed Sep. 28, 2007, and claims priority to U.S. Provisional Patent Application Ser. No. 60/848,351 filed Sep. 29, 2006. The entire contents of both applications are herein incorporated by reference.

BACKGROUND

Laser scanning microscopes (such as two-photon and confocal microscopes) are widely used for acquiring images of narrow sections of cells and tissues, in which molecules of interest are tagged with fluorescent molecules, so that the latter render the former visible through emission of light. By acquiring multiple images of such thin sections, three-dimensional images of the samples can be obtained. In experiments involving fluorescence tagging with multiple colors, such as in studies of protein co-localization or protein-protein interactions (studied through Fluorescence Resonance Energy Transfer—FRET—which involves at least two different tags), a fourth dimension becomes necessary, i.e., the spectral dimension (i.e., the wavelength of the emitted light).

SUMMARY

Various detection schemes for spectral properties have been implemented in most commercial confocal microscopes. However, confocal microscopes may suffer from some or all of the following problems, when compared to two-photon microscopes: (1) low acquisition speeds, mostly due to use of a point-scan method; (2) photodestruction (bleaching) of fluorescent light (while the signal is only read from a thin layer), and long time necessary to excite the sample, due to slow reading of the multiple wavelengths at each point; and (3) low signal-to-noise ratio, due to the fact that excitation and emission happen at wavelengths close to one another, making filtering of the signal difficult. On the other hand, known two-photon microscopes, which avoid problems (2) and (3) above, either do not present spectral resolution at all, or, when they do, they suffer from slow acquisition speed.

In one form, the invention provides a microscope for generating an image of a sample, the microscope comprising: a light source for generating a pulsed light; a scanning mirror receiving the pulsed light and transmitting the pulsed light to the sample to be imaged causing the sample to emit energy; a dispersive element that receives the emitted energy from the sample, disperses the energy into its spectral elements and transmits the spectrally dispersed energy; and a camera that generates a spectrally resolved image of the sample based on the spectrally dispersed energy from the dispersive element The invention also provides a method of generating an image of a sample having x and y dimensions and using a microscope having a laser light source, a computer controlled scanning mirror, a dispersive element and a camera, the method comprising: generating laser energy; scanning the laser energy across the sample to cause emission of light from the sample; dispersing the light emitted from the sample into its spectral elements; and generating a spectrally resolved image of the sample at a given wavelength.

The present invention seeks to produce spectrally resolved fluorescence images of samples using a two-photon microscope after only one full scan of the sample, and avoid all of the problems mentioned above.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Figure 1:
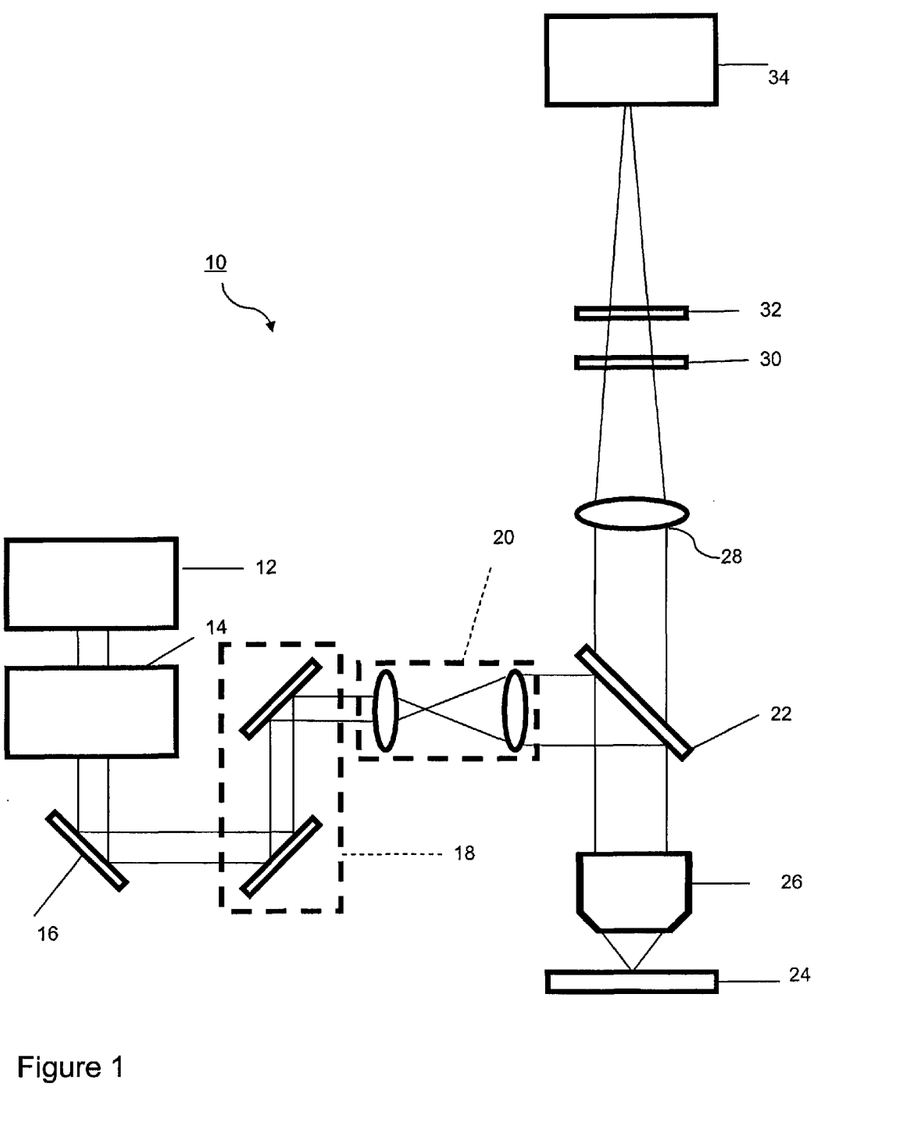
FIG. 1 is a schematic representation of a microscope 10 embodying the invention.

FIG. 1 shows one form of a two-photon microscope 10 with spectral resolution embodying the present invention. The microscope 10 includes a high power solid state laser 12. In one embodiment, the laser 12 is a Verdi brand laser produced by Coherent Inc, and operating at five watts to provide continuous wave (CW) light at a wavelength of 532 nanometers (nm). Other embodiments can employ different lasers operating in different formats as appropriate. The light generated from laser 12 is used to pump a modelocked Ti:Sapphire laser 14. In one embodiment, the Ti:Sapphire laser 14 is a Kapteyn-Murnane Labs laser, of course, other suitable brands may be substituted. The Ti:Sapphire laser 14 generates femtosecond pulses of near-infarared infrared light (centered at approximately 800 nm with a bandwidth of 120 nm). The output of the laser 14 is steered by fixed mirror 16 as well as two computer-controlled, x-y scanning mirrors 18 (x and y here refer to two mutually orthogonal directions on the sample and the corresponding directions on the detector 34). In one embodiment the computer-controlled, x-y scanning mirrors 18 are a pair of mirrors attached to galvanometric scanners (10 mm aperture) that are produced by Nutfiled Technology. The beam of light is then expanded by telescope 20, and passed to a short-pass dichroic mirror 22. Telescope 20 has a conventional round lens which focuses the beam to a point.

Short-pass dichroic mirror 22 reflects the light in the focused beam with a long wavelength, and transmits the light in the beam having a shorter wavelength (in this embodiment, light in the visible spectrum). The beam of light is then focused to a diffraction-limited spot on the sample to be imaged 24 by an infinity-corrected high numerical aperture objective 26.

As the diffraction-limited spot is scanned across the sample 24 in the x-direction by the x-y scanning mirrors 18, the back-propagating fluorescence emission from the sample is collected by the objective 26, sent through the short-pass dichroic mirror 22, the tube lens 28, the short-pass filter 30, and is dispersed into spectral components by a light dispersive element 32, in this embodiment, an optical grating. The dispersed beam is projected onto the two-dimensional charge coupled device ("CCD") detector 34. The terms detector, CCD detector, camera and CCD camera are used interchangeably herein. The short-pass dichroic mirror 22 allows visible light to pass through while reflecting most of the infrared light. The short-pass filter 30 rejects any residual infrared component in the back-propagating light, which would otherwise overwhelm the visible components of interest. The spectral components of the fluorescence emission from the scanned spot are dispersed by the optical grating 32 to form a line on the CCD detector 34 corresponding to each scanned spot (or x position on the sample). In one embodiment of the invention (not shown), a transmission grating is used as the dispersive element 32, but a reflection grating can also be used as the dispersive element 32. Also, in other embodiments (also not shown), it is possible to use a prism as dispersive element 32, as well as any other spectral element capable of dispersing the spectral components of the fluorescence emission from the scanned spot.

Using scanning mirrors 18, the laser light is directed across the sample (along, for example, the x-direction) such that the fluorescence emission spectrum sweeps across the detector 34 to form a rectangle. One dimension of this rectangle corresponds to the scanning direction, with the emission spectrum at each point spread out in the other dimension. In other words, the x-direction on the detector 34 still corresponds to the x-direction on the sample, but the y-direction on the detector 34 corresponds to the spectral dimension (i.e., wavelength) of the sample rather than the y-direction of the sample. One two-dimensional image is captured for each line scanned on the sample in which the x-dimension corresponds to the actual x-dimension of the sample, and the y-dimension corresponds to the spectral dimension (wavelength). Scanning the laser across the sample in the x-direction creates a full image of the spectral components of the fluorescence emission for that y-position. A computer (not shown) is connected to the ccd camera, and the full spectral image is stored in the computer for each position in the y-direction. After performing line scans for different y-values of the sample (through control of the x-y scanning mirrors 18), and storing the images in the computer, the resultant images are reconstructed (as described below) to give the final spectrally resolved fluorescence images.

Figure 2:
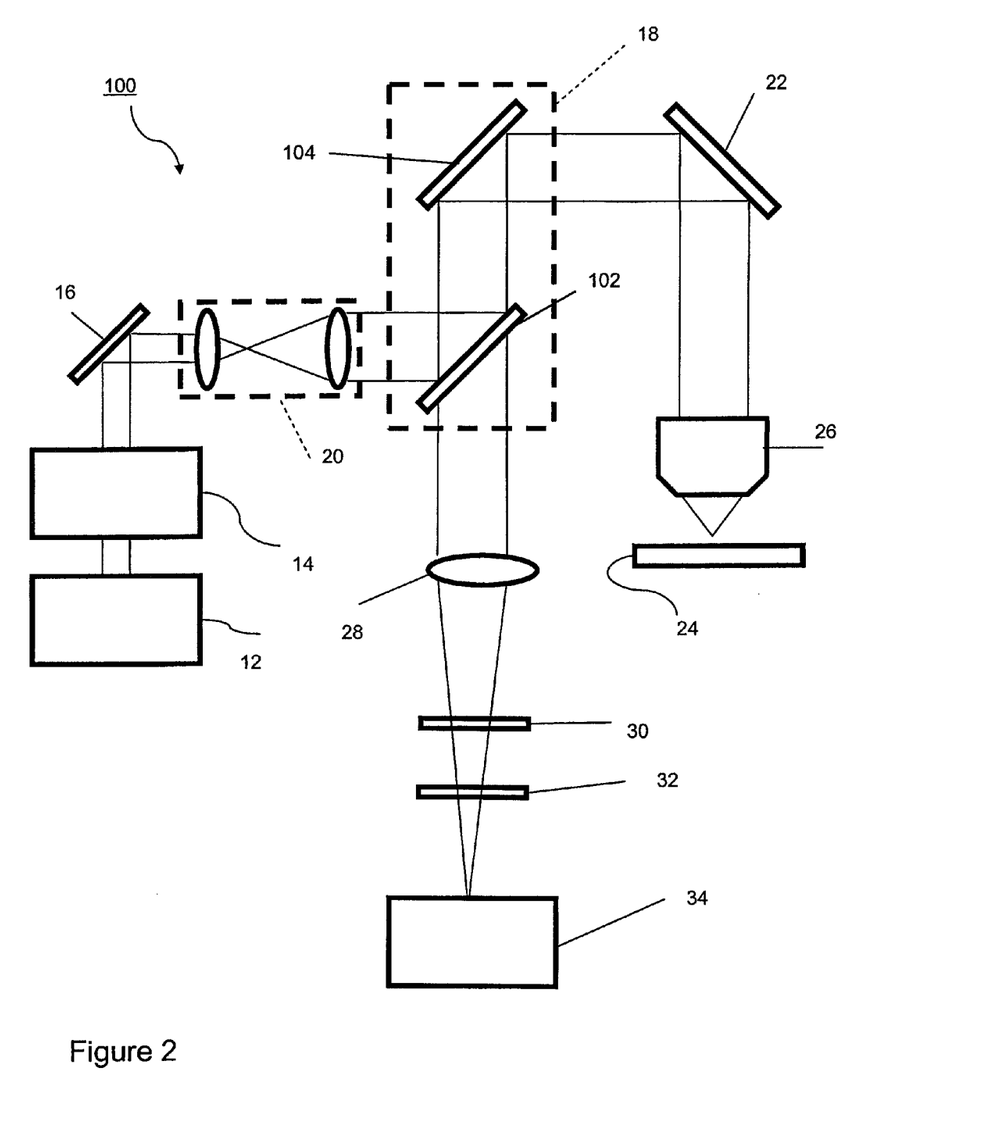
FIG. 2 is a schematic representation of another microscope 100 embodying the invention.
Figure 3:
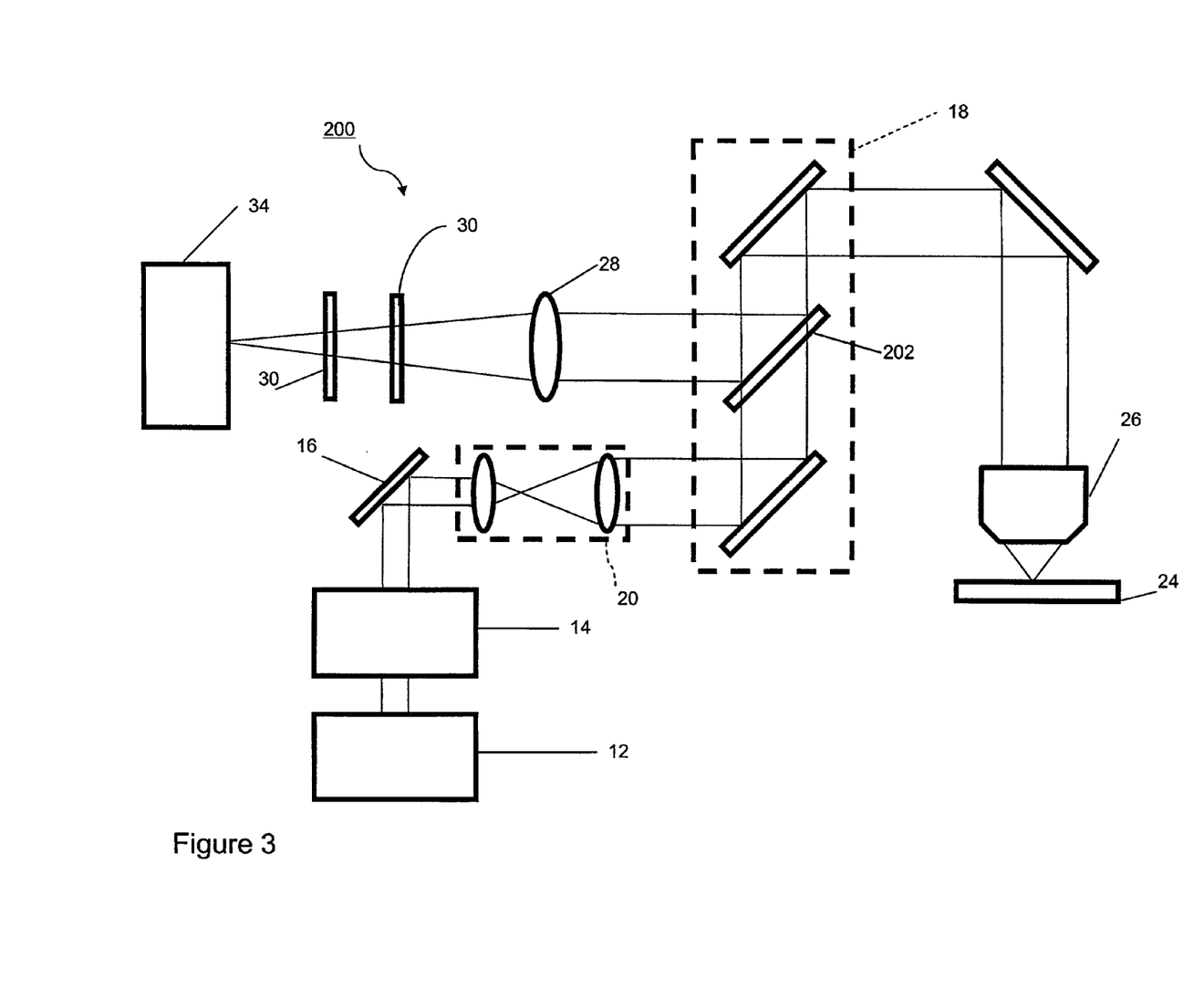
FIG. 3 is a schematic representation of yet another microscope 200 embodying the invention.
Figure 4:
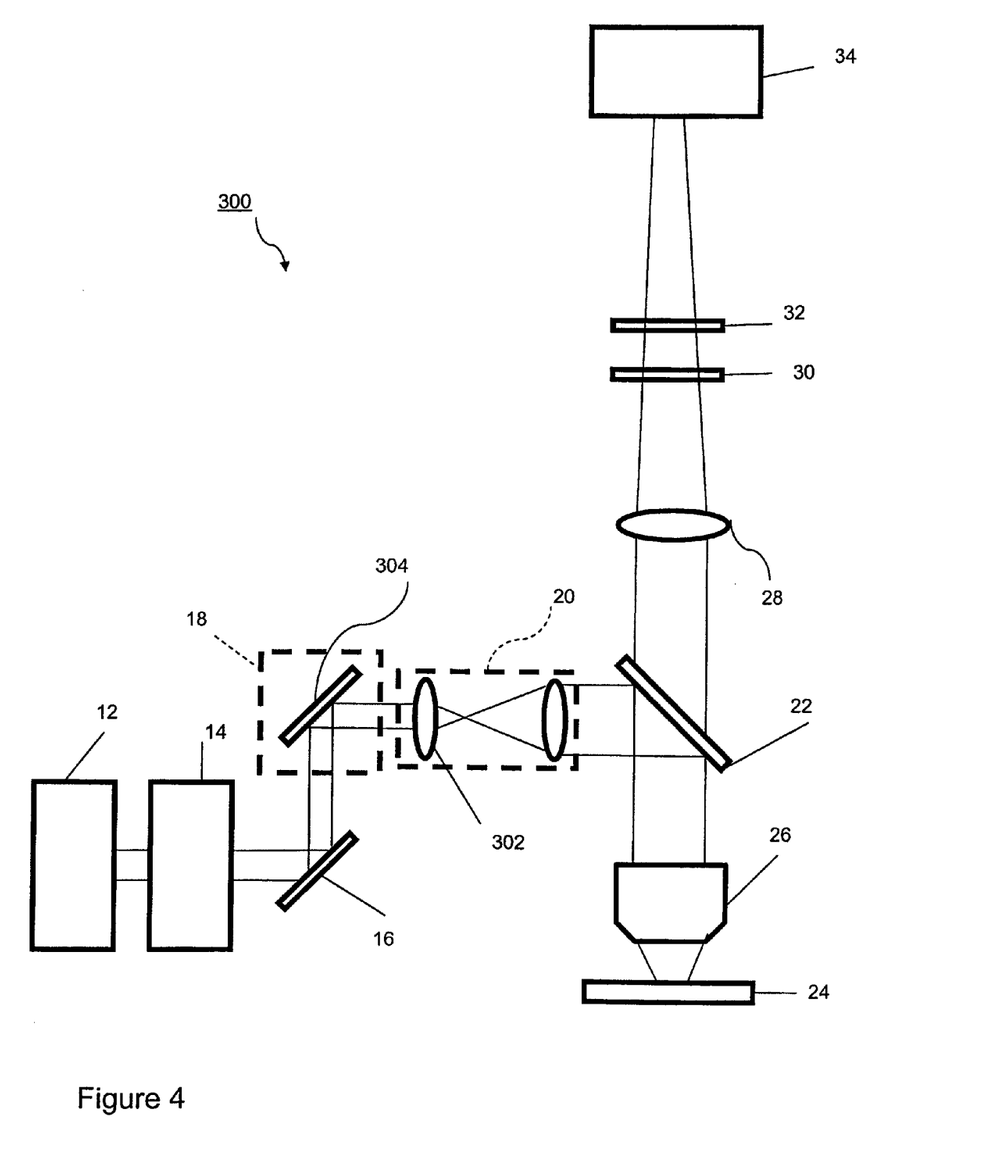
FIG. 4 is a schematic representation of yet another microscope 300 embodying the invention.

FIGS. 2 and 3 illustrate two additional embodiments of the invention 100 and 200, respectively. Like parts are identified using like reference numerals. As shown in FIG. 2, the microscope 100 includes a short-pass, dichroic mirror 102 used as one of the computer-controlled, scanning mirrors 18. This results in a half-descanned detection. That is, the back-propagating light is made immobile in the direction controlled by the top scanning mirror 104. FIG. 3 shows yet another microscope 200 embodying the invention and employing half-descanned detection. Microscope 200 includes a long-pass dichroic mirror 202 is inserted between the two scanning mirrors 18. Long-pass dichroic mirror 202 is used here so that only the visible components of the back-propagating light are sent to the detector 34. Similar to the design shown in FIG. 2, the back-propagating light is made immobile in the direction controlled by the top scanning mirror FIG. 4 illustrates another microscope 300 embodying the invention. Again, like parts are identified using like reference numerals. As shown in FIG. 4, a cylindrical lens 302 is used in telescope 20, so that the focused beam is a line (e.g., along the x-axis of the sample), instead of a point. The line lying along the x-axis is scanned by a single scanning mirror 304 in the y-direction. The emission spectra for each sample point across the line remain aligned along the y-axis and are acquired simultaneously by the CCD detector 34 in a single run. In this way, the time necessary for the other designs to scan the focal point along the x-direction (which involves repeated communication with a computer) is reduced to the time it typically takes to acquire a single point. This leads to a significant increase in the acquisition speed.

Figure 5:
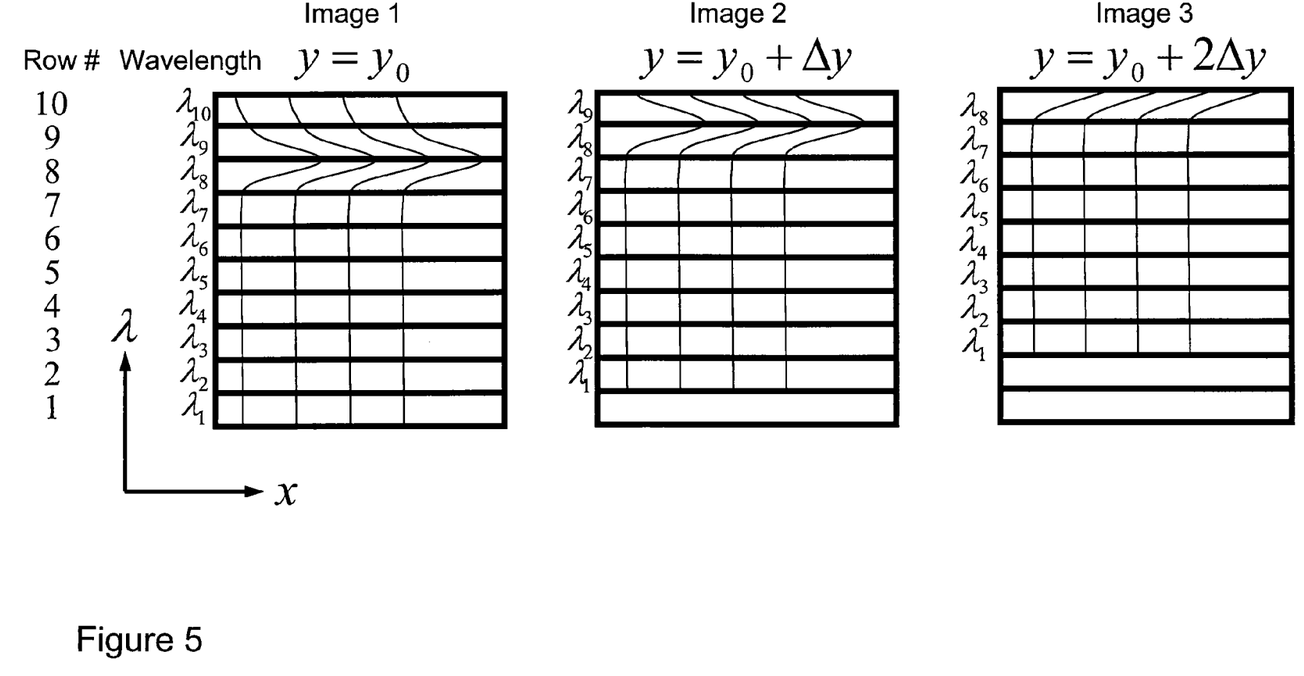
FIG. 5 is a series of plots generated in a calibration procedure and showing the relationship between rows of image pixels and the corresponding spectral dimension (wavelength).
Figure 6:
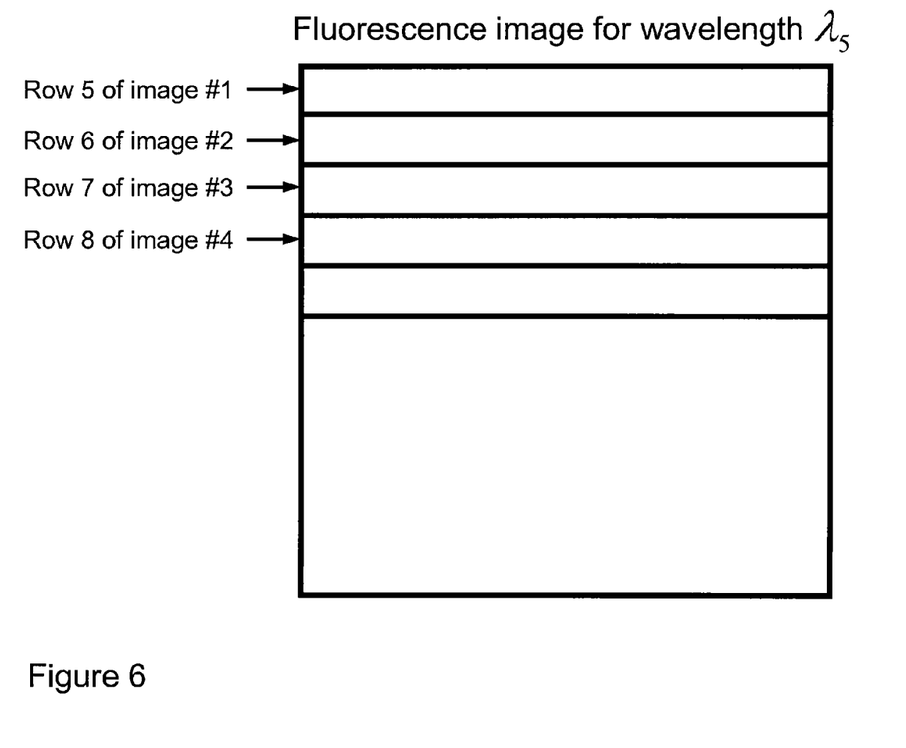
FIG. 6 illustrates the procedure for reconstructing an image of the fluorescence emission of the sample at a wavelength of interest.
Figure 7:
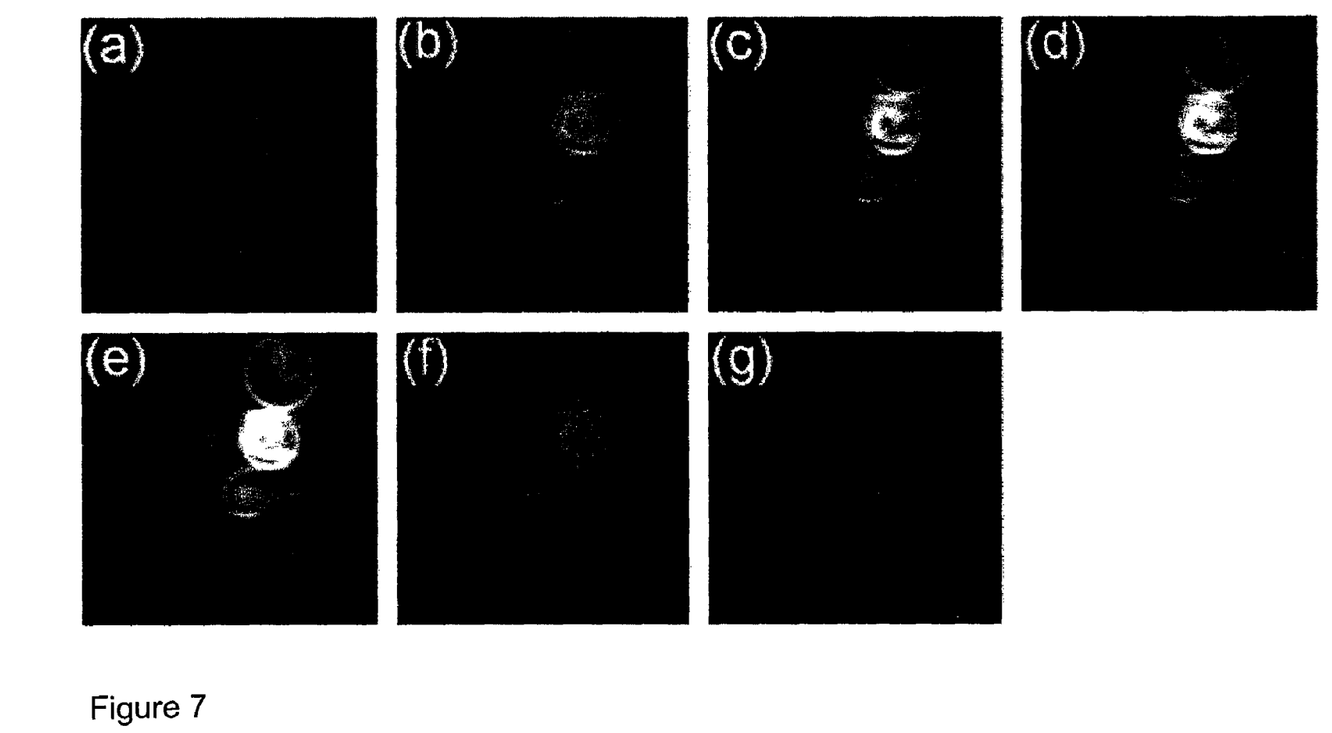
FIG. 7 is a series of spectrally-resolved images acquired using the microscope shown in FIG. 1.

The reconstruction procedure (which is performed by the computer) is illustrated in FIGS. 5 and 6. To obtain the fluorescence emission image for a particular wavelength, let us say, $\lambda_5$, one finds the row number on the first image (i.e., the spectrally resolved image corresponding to the first y-position on the sample) that corresponds to the desired wavelength (row five in this example). The desired wavelength may be chosen based on knowledge of the particular wavelength at which the sample fluoresces. Alternatively, the images can be spectrally resolved at all wavelengths if there is insufficient knowledge to target a specific wavelength. Still referring to FIG. 5, the next row of the next image (i.e., row six on the second image) would, by virtue of the calibration procedure, correspond to the same wavelength but correspond to the next y-value, and so on. Stacking all the image rows that correspond to the wavelength of interest, an image of the fluorescence emission of the sample at the wavelength of interest is obtained. This procedure is then repeated for other wavelengths. Spectrally-resolved images acquired with the preferred implementation of the invention are shown in FIG. 7. These images show yeast cells expressing a membrane receptor (Sterile 2-alpha factor protein ("Ste2p")) tagged with a fluorescent tag (Green Fluorescent Protein ("GFP")).

By using a standard sample that fluoresces uniformly across the sample (e.g., fluorescein), the line-scanning procedure can be calibrated so that from line-scanning at one y-value to the next on the sample, let us say, from $y=y_0$ to $y=y_0+\Delta y$, the fluorescence spectrum moves by exactly one pixel along the spectral dimension on the detector 34. This calibration procedure also allows identification of the relation between row numbers and wavelengths on each of the images as shown in FIG. 5. When the back-propagating light is made immobile in the y-direction (such as with the microscopes 100 and 200), the fluorescence spectra will be immobile on the detector. In this case, the reconstruction procedure is very straightforward, since a particular row always corresponds to the same wavelength in all the images and so no calibration is required. In these embodiments, a dichroic mirror replaces the scanning mirror or is positioned in the narrow space between the scanning mirrors.

In any of the embodiments described, one full scan of the sample gives spectrally resolved fluorescence images of the sample. This can lead to a tremendous increase in acquisition speed when fast detectors 34 are used. All of the embodiments also allow for transmission imaging. The only modification required is to provide a broadband light source beneath the sample stage and a narrow band-pass filter (such as an interference filter) in the optical path somewhere between the sample and the detector 34. Without the band-pass filter, multiple "ghost" images of the sample may be projected onto the detector 34 due to the grating. The band-pass filter removes all but one of these images.

The embodiments described herein provide for much faster acquisition of spectrally resolved images than known microscopes. Specifically, the acquisition speed for the point-scan configuration can be, theoretically, at least fifty times higher than that of confocal microscopes. Speeds of about three times higher (thirty seconds compared to ninety seconds) than that of a Leica confocal microscope have been achieved while acquiring images at ten times the number of distinct wavelengths (i.e., ten times higher spectral resolution). In addition, the line-scan design should allow a much higher speed, theoretically at least a factor of five times better than the point-scan (i.e., close to video-rate acquisition speed), due to removal of the x-scanner, the speed of which is limited by its mechanics and the necessity of communicating with the computer controlling the scanner. Moreover, the microscopes described also allow for transmission imaging.

Various features and advantages of the invention are set forth in the following claims.

The invention claimed is:

1. A microscope for generating a multi-dimensional, spectrally resolved image of a sample, the microscope comprising:
   a light source for generating a pulsed light;
   an optical scanner receiving the pulsed light and transmitting the pulsed light to focal points of the sample to be imaged, and causing a molecule at each focal point to absorb two infrared photons and emit energy;
   a dispersive element that receives the emitted energy from a single scan of the sample, disperses the energy into its spectral elements and transmits the spectrally dispersed energy; and
   a camera that generates the multi-dimensional, spectrally resolved image of the sample based on the spectrally dispersed energy from the dispersive element using only the emitted energy from the single scan of the sample.

2. The microscope as claim 1, wherein the multi-dimensional, spectrally resolved image is a two-dimensional image of the sample, in which one dimension is a line scanned along a geometrical dimension of the sample and another dimension includes wavelengths of the spectrally dispersed energy from the dispersive element.

3. The microscope as claim 1, wherein the dispersive element receives the emitted energy from the sample without the emitted energy passing through a physical aperture.

4. The microscope as claim 1, wherein rows of the multi-dimensional, spectrally resolved image are combined with rows of other multi-dimensional, spectrally resolved images generated by the camera to form a multi-dimensional image at a particular wavelength in which a first dimension corresponds to the geometrical dimension of the sample and a second dimension corresponds to a second geometrical dimension of the sample.

5. The microscope as claim 1, wherein the optical scanner comprises a plurality of computer controlled mirrors, and wherein one of the computer controlled mirrors is a short pass, dichroic mirror.

6. The microscope as claim 1, wherein the optical scanner comprises a pair of computer controlled scanning mirrors and a long pass dichroic mirror positioned between the pair of computer controlled scanning mirrors.

7. The microscope as claim 1, wherein the dispersive element comprises one of a transmission grating and a prism.

8. The microscope as claim 1, further comprising a round lens for focusing the pulsed light from the light source to the focal points.

9. The microscope as claim 1, further comprising a cylindrical lens for focusing the pulsed light from the light source to the focal points along a line at a y-position of the sample.

10. The microscope as claim 1, further comprising a broadband light source positioned beneath the sample to be imaged and a narrow band-pass filter positioned between the sample and the camera to provide transmission imaging of the sample.

11. A method of generating a spectrally resolved image of a sample having x- and y-dimensions and using a microscope having a laser light source, a computer controlled scanning optical scanner, a dispersive element and a camera, the method comprising:
    generating laser energy with the laser light source;
    scanning the laser energy across a plurality of focal points of the sample to cause a molecule at each focal point to absorb two-infrared photons and, in response, emit light;
    dispersing the light emitted from each focal point of the sample into spectral elements by passing the light through one of a transmission grating and a prism; and
    generating a series of spectral images, each spectral image corresponding to a y-position on the sample, based on a single scan of each focal point.

12. The method of claim 11, further comprising constructing a spectrally resolved image with x- and y-dimensions corresponding to the x- and y-dimensions of the sample by selecting and combining portions of each spectral image of the series of spectral images, wherein the selecting is based on a wavelength depicted in the selected portion.

13. The method of claim 12, wherein the spectrally resolved image depicts a particular wavelength of the light energy from each x-y position of the sample.

14. The method of claim 12, wherein each row of the spectrally resolved image is obtained from a different spectral image of the series of spectral images, and each spectral image depicts the light emitted at multiple wavelengths, at multiple x-positions of the sample, and at one y-position of the sample.

15. The method of claim 11, wherein the emitted light from the sample is received by the dispersive element without first passing through a physical aperture.

16. The method of claim 12, wherein the sample further comprises a z-dimension and wherein
    generating the series of spectral images further includes generating spectral images corresponding to a plurality of z-positions on the sample, and
    constructing the spectrally resolved image further includes constructing the spectrally resolved image to have x-, y-, and z-dimensions corresponding to the x-, y-, and z-dimensions of the sample by selecting and combining portions of each spectral image of the series of spectral images.

17. A method of generating an image of a sample having x- and y-dimensions and using a microscope having a laser light source, a computer controlled optical scanner, a dispersive element and a camera, the method comprising:
    generating laser energy with the laser light source;
    focusing the laser energy on focal points along a y-position of the sample simultaneously to cause molecules at the focal points to absorb two-infrared photons and emit light;

adjusting the computer controlled optical scanner to focus the laser energy on additional focal points along additional y-positions of the sample to complete a single scan of the sample;

dispersing the light emitted from the sample into its spectral elements;

receiving the spectral elements of the dispersed light as a continuous spectrum; and generating a series of spectral images, each spectral image corresponding to a y-position on the sample, based on a single scan of each focal point.

18. The method of claim 17 wherein dispersing the light from the sample into its spectral elements comprises passing the light through one of a transmission grating and a prism.

19. The method of claim 17, further comprising constructing a spectrally resolved image with x- and y-dimensions corresponding to the x- and y-dimensions of the sample by selecting and combining portions of each spectral image of the series of spectral images, wherein the selecting is based on a wavelength depicted in the selected portion.

20. The method of claim 19, wherein each row of the spectrally resolved image is obtained from a different spectral image of the series of spectral images, and each spectral image depicts the light emitted at multiple wavelengths, at multiple x-positions of the sample, and at one y-position of the sample.

21. The method of claim 19, wherein the sample further comprises a z-dimension and wherein generating the series of spectral images further includes generating spectral images corresponding to a plurality of z-positions on the sample, and constructing the spectrally resolved image further includes constructing the spectrally resolved image to have x-, y-, and z-dimensions corresponding to the x-, y-, and z-dimensions of the sample by selecting and combining portions of each spectral image of the series of spectral images.

* * * * *